(12) United States Patent
Karlsson et al.

(10) Patent No.: US 11,662,290 B2
(45) Date of Patent: May 30, 2023

(54) FLEXIBILITY MEASUREMENTS OF INJECTABLE GELS

(71) Applicant: GALDERMA HOLDING SA, La Tour-de-Peilz (CH)

(72) Inventors: Morgan Karlsson, Knivsta (SE); Åke Öhrlund, Uppsala (SE)

(73) Assignee: Galderma Holding SA, Zug (CH)

( * ) Notice: Subject to any disclaimer, the term of this patent is extended or adjusted under 35 U.S.C. 154(b) by 1000 days.

(21) Appl. No.: 16/466,364

(22) PCT Filed: Dec. 7, 2017

(86) PCT No.: PCT/EP2017/081783
§ 371 (c)(1),
(2) Date: Jun. 4, 2019

(87) PCT Pub. No.: WO2018/104426
PCT Pub. Date: Jun. 14, 2018

(65) Prior Publication Data
US 2020/0072721 A1 Mar. 5, 2020

Related U.S. Application Data

(60) Provisional application No. 62/431,093, filed on Dec. 7, 2016.

(51) Int. Cl.
*G01N 11/16* (2006.01)
*A61L 27/20* (2006.01)
(Continued)

(52) U.S. Cl.
CPC ............ *G01N 11/165* (2013.01); *A61L 27/20* (2013.01); *A61L 27/52* (2013.01); *A61L 27/58* (2013.01);
(Continued)

(58) Field of Classification Search
CPC .... G01N 11/165; G01N 11/16; G01N 11/162; G01N 11/142; G01N 2011/0026;
(Continued)

(56) References Cited

U.S. PATENT DOCUMENTS

2015/0084232 A1 3/2015 Rutz et al.

FOREIGN PATENT DOCUMENTS

CN 1843606 * 10/2006
WO 2016150974 A1 9/2016

OTHER PUBLICATIONS

International Preliminary Report on Patentability on PCT Appl. Ser. No. PCT/EP2017/081783 dated Jun. 11, 2019 (8 pages).
(Continued)

*Primary Examiner* — Robert R Raevis
(74) *Attorney, Agent, or Firm* — Sunit Talapatra; Foley & Lardner LLP

(57) ABSTRACT

A process for evaluating rheological characteristics of an injectable gel including measuring the flexibility, wherein the flexibility is evaluated by measuring the strain at the crossover point of the amplitude sweep. The process may include subjecting an injectable gel to oscillating mechanical stresses to determine G' and G" as a function of strain (γ) in an amplitude sweep, determining the crossover point as the point at which G' and G" have the same value, determining the strain $\gamma_{cross}$ at the crossover point, and determining the flexibility of the injectable gel as $\gamma_{cross}$ or proportional to $\gamma_{cross}$. Further, a method of comparison of dermal fillers by measuring their flexibility and a method of evaluation of dermal filler behavior in human skin by measuring the flexibility.

12 Claims, 5 Drawing Sheets

(51) Int. Cl.
    *A61L 27/52*    (2006.01)
    *A61L 27/58*    (2006.01)
    *G01N 11/14*    (2006.01)
    *G01N 11/00*    (2006.01)
    *A61K 31/728*    (2006.01)
    *G06F 9/44*    (2018.01)
    *A61L 27/50*    (2006.01)

(52) U.S. Cl.
    CPC .......... *G01N 11/142* (2013.01); *G01N 11/16* (2013.01); *G01N 11/162* (2013.01); *A61K 31/728* (2013.01); *A61L 27/50* (2013.01); *A61L 2400/06* (2013.01); *A61L 2430/34* (2013.01); *G01N 2011/0026* (2013.01); *G06F 9/44* (2013.01)

(58) Field of Classification Search
    CPC .......... A61L 27/20; A61L 27/52; A61L 27/58; A61L 2400/06; A61L 2430/34; A61L 27/50; A61K 31/728; G06F 9/44
    USPC ....... 73/53.01, 54.02, 64.41–64.43, 760, 866
    See application file for complete search history.

(56) References Cited

OTHER PUBLICATIONS

Sein et al., "Rheological Characterization, Crystallization, and Gelation Behavior of Monoglyceride Gels", Journal of Colloid and Interface Science, vol. 249, No. 2, 2002, (pp. 412-422).

International Search Report and Written Opinion issued in corresponding International Patent Application No. PCT/EP2017/081783, 11 pages (dated Apr. 6, 2019).

Franck, A., "Understanding Rheology of Structured Fluids," TA Instruments, AAN016, Retrieved from the Internet: URL: http://www.tainstruments.com/pdf/liter, 11 pages, (Jun. 5, 2013).

Hvidt, S., "Yield Stress Value Determinations of a Physical Gel," Annual Transactions of the Nordic Rheology Society, Department of Chemistry-NSM, Roskilde University, Denmark, vol. 21, pp. 311-314, (Jan. 1, 2013).

\* cited by examiner

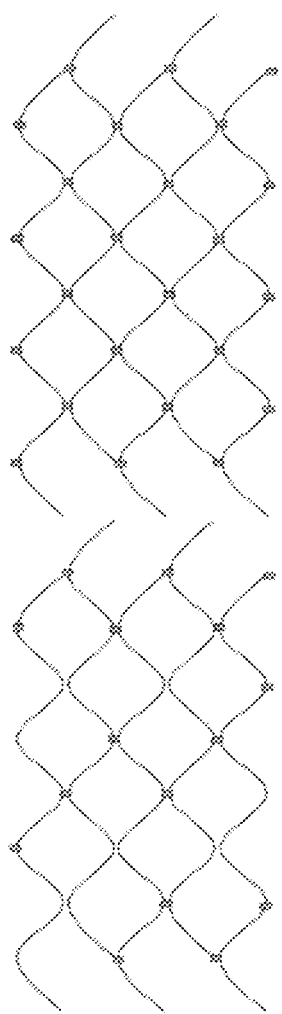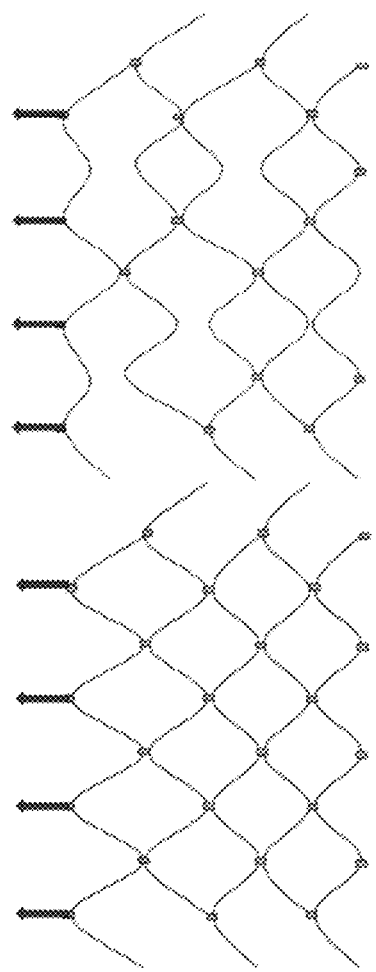

FLEXIBILITY MEASUREMENTS OF INJECTABLE GELS

TECHNICAL FIELD OF THE INVENTION

The present invention relates to the field of polysaccharide gels. More specifically, the present invention relates to a process to characterize an injectable gel.

BACKGROUND TO THE INVENTION

One of the most widely used biocompatible polymers for medical use is hyaluronic acid. It is a naturally occurring polysaccharide belonging to the group of glycosaminoglycans (GAGs). Hyaluronic acid (HA) and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

It is important to have tools for characterizing the mechanical properties of an injectable gel in the laboratory since it may avoid or decrease the number of in vivo tests needed when evaluating the performance of a gel.

An example of a method for characterizing a gel is shown in WO 2016150974, which discloses a method for evaluating the mechanical performance of a filler gel. A sample gel is subjected to oscillating mechanical stresses to determine the elastic modulus G' and a score is derived from the integration of G'.

However, there is a need in the art for improved methods of determining the mechanical properties of a gel

SUMMARY OF THE INVENTION

It is an object of the present invention to provide simplified means for characterizing an injectable gel in vitro.

As a first aspect of the invention, there is provided a process for evaluating rheological characteristics of an injectable gel comprising measuring the flexibility, wherein the flexibility is evaluated by measuring the strain at the crossover point of the amplitude sweep.

As a complementary aspect, there is provided a process for evaluating rheological characteristics of an injectable gel consisting of measuring the flexibility, wherein the flexibility is evaluated by measuring the strain at the crossover point of the amplitude sweep.

Thus, the first aspect of the invention relates to a process to characterize an injectable gel, and more preferably a dermal filler gel, by measuring a new parameter, the flexibility. The flexibility of the gel is a feature that is displayed after injection, when the dermal filler gel has settled in the tissue. The flexibility gives the ability to natural animation without the implant showing under the skin. The gel follows the movement of the face and gives the ability to preserve the natural expressions of the face.

In the dermal filler domain, there is still a need to scientifically characterize the injectable product in order to understand and explain their behavior into the body or skin after injection. This new parameter will bring high values to characterization of dermal filler, more preferably a dermal filler containing cross linked hyaluronic acid.

The flexibility value of the injectable gel may be the actual crossover point or a value that is proportional to the crossover point.

The inventors have thus found that the investigation of the flexibility of an injectable gel is important since this may give information on how the gel will behave and function after injection. The inventors have found that injectable gels having the same degree of crosslinking may have different measured flexibility, and that the flexibility may be a good parameter to use when evaluating if a gel is suitable for injection e.g. in the facial area of a patient. A more flexible gel may be able to follow the movements of the surrounding tissue to a better degree compared to a less flexible gel.

Measuring the flexibility according to the present disclosure is further advantageous in that it gives a measure that is not only dependent on the elastic modulus G' alone, but instead takes into account both the elastic modulus G' and the viscous modulus G". Thus, the flexibility value as measured in the present disclosure takes into account several rheological parameters and is thus believed to give a better measure of the viscous properties of an injectable gel.

The method of the present disclosure is further believed to be a versatile way of measuring a flexibility value and is further less complex compared to prior art methods that e.g. comprises integrating a function of G'.

As an example, the crossover point of the amplitude sweep is the point where the elastic modulus G' and the viscous modulus G" have the same value.

In the present application, G' and G" will be used and are defined as follows: G', is the elastic modulus. It describes the resistance of the gel to elastic deformation, the firmness of the product, and is expressed in Pa (Pascal). A strong gel will give a larger number compared to a weak gel.

G" is the viscous modulus. It describes the resistance of the gel to viscous deformation, and is expressed in Pa (Pascal). Together with G', it describes the total resistance to deformation.

Amplitude sweeps and frequency sweeps refer to oscillary rheological test and are known to the skilled person for determining G' and G" as a function of strain of a gel. Thus, by subjecting a specimen to an oscillatory stress and determining the response, both the elastic and viscous or damping characteristics as a function of stress or strain can be obtained. The stress is the force causing the deformation divided by the area to which the force is applied, whereas the strain may be referred to as the relative deformation compared to an original state of the specimen.

The test may be performed by introducing a probe into the gel. The cone may be forced into oscillatory shear (angular frequency $\omega$) or rotation.

During an amplitude sweep the amplitude of the deformation—or alternatively the amplitude of the shear stress—is varied while the frequency is kept constant. The amplitude is the maximum of the oscillatory motion. For the analysis, the storage modulus G' and the loss modulus G" are plotted against the deformation.

In embodiments of the first aspect of the invention, the process comprises
  subjecting an injectable gel to oscillating mechanical stresses to determine G' and G" as a function of strain ($\gamma$) in an amplitude sweep,
  determining the crossover point as the point at which G' and G" have the same value,
  determining the strain $\gamma_{cross}$ at the crossover point, and
  determining the flexibility of the injectable gel as $\gamma_{cross}$ or proportional to $\gamma_{cross}$.

As an example, the amplitude sweep may be performed by increasing the amount of deformation of the gel until a change in both G' and G" are observed.

The step of determining the crossover point $\gamma_{cross}$ from the measured G' and G" as a function of strain ($\gamma$) may be performed in different ways. As an example, functions G'($\gamma$)

and G"(γ) may be fitted to the experimental data and $\gamma_{cross}$ may be determined by solving G'(γ)=G"(γ). However, $\gamma_{cross}$ may be determined in a visual manner.

Thus, as an example wherein the step of determining the crossover point as the point at which G' and G" have the same value is performed by plotting G' and G" as a function of the strain (γ) and selecting the crossover point as the point where the plot of G' and the plot of G" intersect.

Performing the amplitude sweep may be preceded by other measures in order to increase the output from the amplitude sweep. Consequently, in embodiments of the first aspect of the invention, the step of determining G' and G" as a function of strain (γ) comprises a step of performing a frequency sweep at a fixed strain before performing the amplitude sweep.

During a frequency sweep the frequency is varied while the amplitude of the deformation—or alternatively the amplitude of the shear stress—is kept constant. For the analysis the storage and loss modulus are plotted against the frequency. The data at low frequencies may describe the behaviour of the samples at slow changes of stress.

In embodiments of the first aspect of the invention, the crossover point is a point outside the linear viscoelastic region (LVR) of the injectable gel.

At low deformation the values of G' and G" may be constant and the sample structure undisturbed. This region is called linear-viscoelastic region (LVR). Thus, the LVR region is the region where the stress changes linearly with deformation and may be at lower strain values. As soon as the moduli start to decrease, the structure is disturbed, and the end of the LVR-region may be reached.

In embodiments of the first aspect of the invention, the flexibility is measured in percentage (%).

The flexibility values for injectable gels may be in the range 0.1% to 20000%, such as in the range 0.1% to 10000%, according to the type of dermal filler analysed.

The flexibility may also be expressed as a dimensionless number, proportional to the percentage. As an example, a flexibility of 100 could be equal to a strain of 1%.

The process of the present invention may be used for evaluating different gels to see if they are suitable for certain applications.

Thus, in embodiments of the first aspect of the invention, the process further comprises the step of comparing the evaluated flexibility with a flexibility value of a reference gel, and if the evaluated flexibility is above said flexibility value of a reference gel, concluding that the injectable gel is more flexible than the reference gel.

As an example, the step of concluding may comprise concluding that the injectable gel is more suitable than the reference gel for being implanted at regions in the face that are subjected to movement.

Further, in embodiments of the first aspect of the invention, the process further comprises the step of comparing the evaluated flexibility with a reference flexibility value, and if the evaluated flexibility is above said reference flexibility value, concluding that the injectable gel is suitable for injection.

Different reference flexibility values may be use depending on the intended use for the gel. As an example, a first reference flexibility value may be used for a first behavior in the skin after injection, and a second reference flexibility value may be used for a second behavior after injection, and the step of concluding may comprise concluding that the gel is suitable for the first application if the measured flexibility is above the first reference flexibility value and suitable for the second application if the measured flexibility is above the second reference flexibility value.

The measured flexibility may as a complement be compared to reference intervals. As an example, a first reference flexibility interval may be used for a first behavior in the skin after injection, and a second reference flexibility interval may be used for a second behavior after injection, and the step of concluding may comprise concluding that the gel is suitable for the first application if the measured flexibility is within the first reference flexibility interval and suitable for the second application if the measured flexibility is within second reference flexibility interval.

In embodiments of the first aspect of the invention, the amplitude sweep is performed at a frequency of between 0.1-10 Hz, such as 0.5 Hz-1.5 Hz. As an example, the amplitude sweep may be performed at a frequency of about 1 Hz.

In embodiments of the first aspect of the invention, the injectable gel is a dermal filler comprising crosslinked hyaluronic acid.

Unless otherwise provided, the term "hyaluronic acid" encompasses all variants and combinations of variants of hyaluronic acid, or hyaluronan, of various chain lengths and charge states, as well as with various chemical modifications That is, the term also encompasses the various hyaluronate salts of hyaluronic acid, such as sodium hyaluronate. Various modifications of the hyaluronic acid are also encompassed by the term, such as oxidation, e.g. oxidation of $CH_2OH$ groups to COOH; periodate oxidation of vicinal hydroxyl groups, optionally followed by reduction or imine formation etc; reduction, e.g. reduction of COOH to $CH_2OH$; sulphation; deamidation, optionally followed by deamination or amide formation with new acids; esterification; substitutions with various compounds, e.g. using a crosslinking agent or a carbodiimide; including coupling of different molecules, such as proteins, peptides and active drug components, to hyaluronic acid; and deacetylation.

As an example, the hyaluronic acid may be a chemically unmodified hyaluronic acid or hyaluronate salt, preferably sodium hyaluronate, having an average molecular weight in the range of 0.5-10 MDa, preferably 0.8-5 MDa, more preferably 1.5-3 MDa or 2-3 MDa. It is preferred that the hyaluronic acid is obtained from non-animal origin, preferably bacteria.

As a second aspect of the invention, there is provided a method of comparison of dermal fillers by measuring their flexibility according to the first aspect above.

In embodiments of the second aspect, the method comprises measuring the flexibility of a plurality of different candidate dermal fillers according to the method of the first aspect of the invention, comparing the measured flexibility between the plurality of candidate dermal fillers, and selecting a dermal filler of the plurality of dermal fillers as a dermal filler suitable for injection based on the comparison.

As an example, the gel having the highest flexibility value may be selected as a dermal filler suitable for injection in the facial area.

A gel having a high measured flexibility may follow the movement of the face and may give the ability to preserve the natural expressions of the face.

The method of comparison may further comprise an initial step of manufacturing a plurality of candidate dermal filler gels in small amount and the selected dermal filler gel suitable for injection may then be manufactured in a greater amount Furthermore, several of the different candidate dermal filler gels may be suitable for injection, e.g. if they have a measured flexibility above a specific reference flexibility value or within a reference flexibility interval.

Thus, the method may comprise the step of determining that a candidate dermal filler gel is suitable for injection if they have a measured flexibility above a specific reference flexibility value or within a reference flexibility interval, and determining that a candidate dermal filler gel is unsuitable for injection if they have a measured flexibility below the specific reference flexibility value or outside a reference flexibility interval.

As a third aspect of the invention, there is provided a method of evaluation of dermal filler behavior in human skin by measuring the flexibility according to the previous aspects above.

As a fourth aspect of the invention, there is provided method for determining a flexibility value of an injectable gel comprising the steps of receiving input data of the elastic modulus G' and the viscous modulus G" as a function of the strain $\gamma$ of said gel, determining the strain $\gamma_{cross}$ as the strain at which the elastic modulus G' and the viscous modulus G" have the same value, determining the flexibility value of the injectable gel as $\gamma_{cross}$ or a value proportional to $\gamma_{cross}$.

The flexibility value of the injectable gel may be the actual crossover point or a value that is proportional to the crossover point.

The method of the fourth aspect of the invention may be performed by a computer program for determining the flexibility from measurement data of the elastic modulus G' and the viscous modulus G".

Receiving input data of the elastic modulus G' and the viscous modulus G" may also comprise plotting G'($\gamma$) and G" ($\gamma$) and/or fitting a function to the data points of G', G" and $\gamma$ to estimate functions G'($\gamma$) and G" ($\gamma$), such as continuous functions G'($\gamma$) and G" ($\gamma$).

The step of determining the strain $\gamma_{cross}$ may comprise calculating the strain $\gamma_{cross}$ by solving for $\gamma$ the equation G'($\gamma$)=G"($\gamma$).

In embodiments of the fourth aspect of the invention, the method is further comprising the step of comparing the flexibility value of the injectable gel with a reference flexibility value.

Further, the method of the fourth aspect of the invention may comprise the step of displaying the flexibility value on a computer screen.

Further, the method of the fourth aspect of the invention may comprise displaying plots of G' and the viscous modulus G" as a function of the strain.

As a fifth aspect of the invention, there is provided a computer program product comprising computer-executable components for causing a device to perform the steps of the method according to the fourth aspect above when the computer-executable components are run on a processing unit included in the device.

BRIEF DESCRIPTION OF THE DRAWINGS

FIG. 5 shows OBT products with fewer (FIG. 5a) and more (FIG. 5b) crosslinking points, while in a relaxed state.

FIG. 6 shows OBT products with fewer (FIG. 6a) and more (FIG. 6b) crosslinking points, while in a stretched state.

DETAILED DESCRIPTION OF THE INVENTION

The present invention relates to a process to characterize an injectable gel, and more preferably a dermal filler gel, by measuring a new parameter, the flexibility.

The flexibility of the gel is measured and in the below description and examples denoted as XStrain. The higher the value is, the higher the flexibility of the gel. This new parameter can be used to characterize different dermal fillers and their different behaviors in skin after injection.

To verify if a difference in flexibility could be detected using a scientific test methodology, rheology was employed. For the first time, the filler flexibility can be measured. As evaluated from the cross-over point between G' and G" in the amplitude sweep results, a difference in flexibility was evident from the difference in the deformation (strain, $\gamma$) at which the cross-over point occurred. The flexibility value obtained is here denoted XStrain. The value of XStrain demonstrates how much deformation the tested material can withstand before changing from a solid-like to a liquid-like behavior, i.e. going from basically reversible to basically irreversible deformation. The XStrain measured can be considered a flexibility index of a material.

The firmness of a product, measured as G' using rheometry, is performed under nearly static conditions. The deformations used in these measurements are very small, in order to keep within the linear viscoelastic region (LVR), the region where the stress changes linearly with deformation. These measurements are normally performed as a frequency sweep. In order to determine a suitable level of deformation to use in the frequency sweep, an amplitude sweep is performed, where the amount of deformation is increased until a change in the results is observed, indicating the end of the LVR. A level of deformation where the measured firmness is stable is chosen for the frequency sweep. However, the data from the amplitude sweep can be further evaluated. When the edge of the LVR is reached, it means that the deformation is so large that the material can no longer retain its original shape, and starts behaving more like a liquid than a solid. In rheology, this point is often referred to as the yield point. A typical example of a material having a noticeable yield point is tomato ketchup, which moves frustratingly little until the bottle is shaken enough, resulting in the delivered portion of ketchup being larger than intended.

Figure 1:
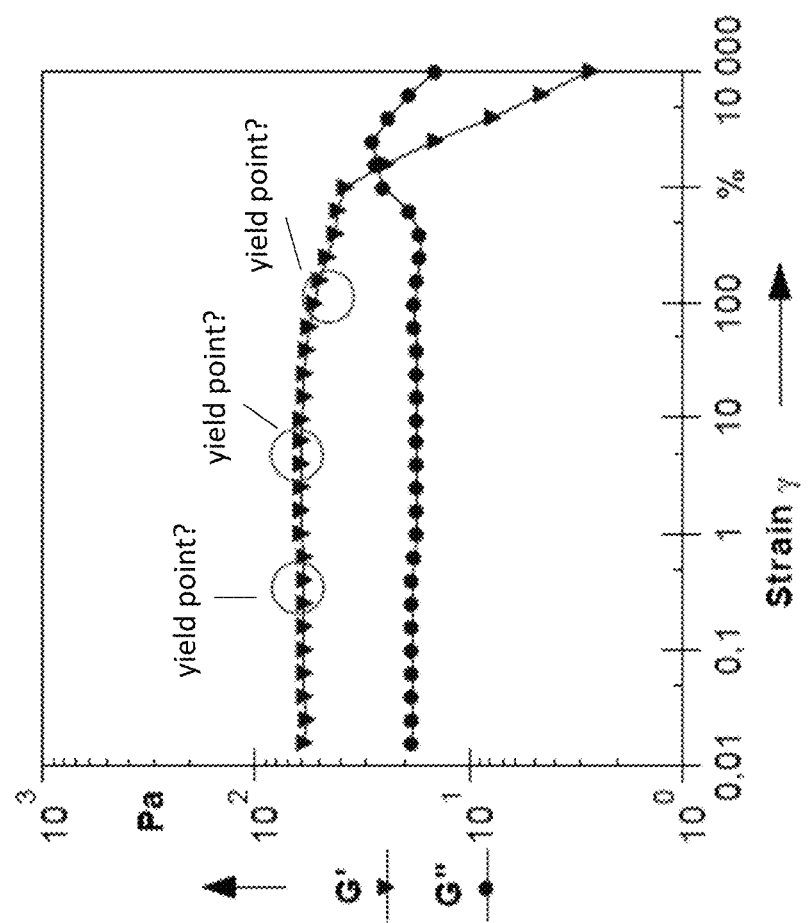
FIG. 1 shows an example of an amplitude sweep showing uncertain yield points.

Though there is a consensus on what the yield point is, the definition on where in the amplitude sweep this can be found may vary. Generally, as soon as there is a change in the signal, e.g. in the level of G', this would indicate the endpoint of the LVR. Since there is always some noise in the signal, the change has to be of a certain magnitude in order to be correctly detected. When analyzing very soft samples giving a weaker signal, a larger deviation has to be allowed in order not to incorrectly detect noise as the end of the LVR (FIG. 1).

Figure 2:
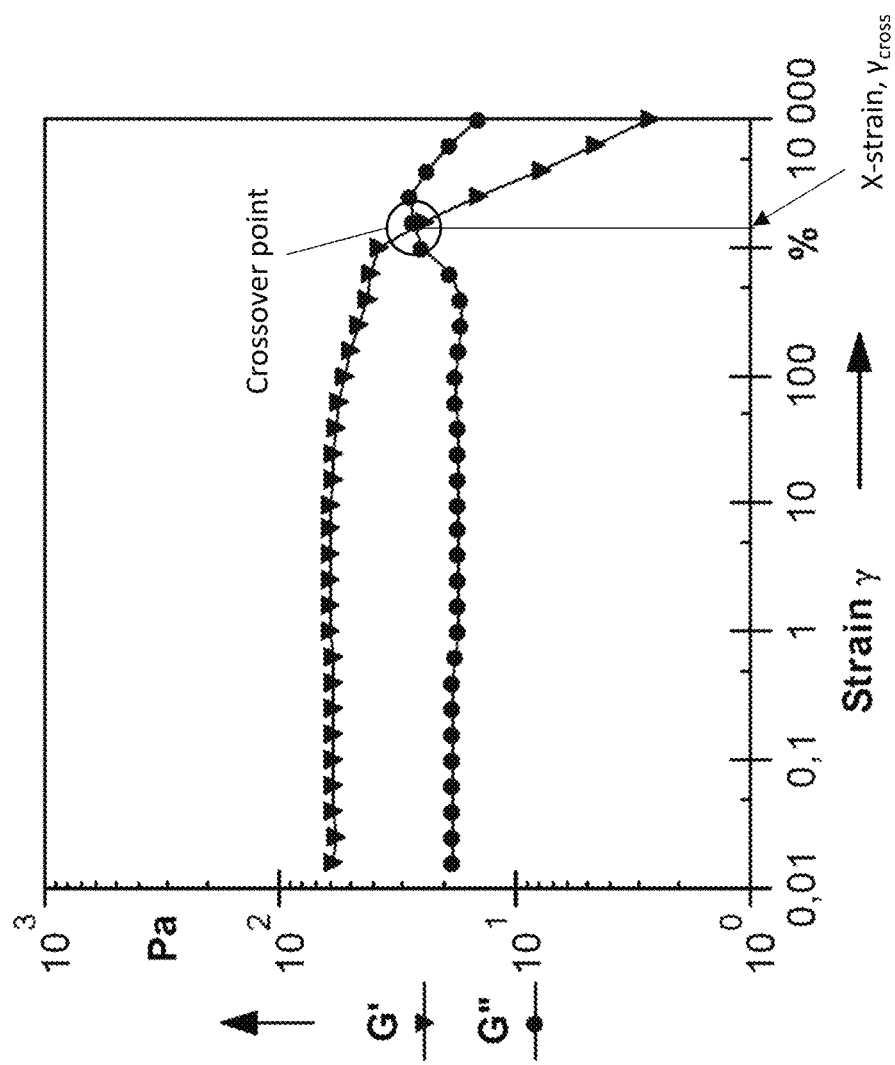
FIG. 2 shows an amplitude sweep with the crossover point.

An endpoint that is much easier to pinpoint exactly is the cross-over point, where G' and G" intersect (FIG. 2). Though this point may be considered to overestimate the yield point, its exactness and simplicity is a huge advantage. The inventors have found that at this cross-over point, the strain can be evaluated as a measure of flexibility. A material with a large XStrain can stand a large deformation before yielding, and can therefore be considered to be more stretchable, or flexible. The cross-over strain value may be considered a flexibility index for the material.

Flexibility values can be in the range of 0.1% to 20000% according to the type of dermal filler requested use.

In a specific embodiment, when dermal filler are injected into the face to correct age related effects, the flexibility parameter gives the ability to natural animation without the implant showing under the skin. Being more of less flexible, the dermal filler hydrogel follows the movement of the face and gives the ability to preserve the natural expressions of the face.

EXPERIMENTAL EXAMPLES

The following non-limiting examples will further illustrate the present invention. In these examples, the flexibility of different dermal fillers comprising hyaluronic acid was determined. The following examples are describing how flexibility can be measured through evaluation of the cross-over point from the amplitude sweep and help to characterize dermal filler products.

Example 1: Measurement of Flexibility a) Injectable Gels

The Optimal Balance Technology (OBT) products from Galderma are dermal filler differing in the amount of crosslinker used. This results in materials with different rheological properties. There is a need to understand their behavior by characterizing their rheological properties, through this measurement of the new parameter: flexibility. The OBT family of dermal filler products has previously been found to cover a large span of G' values as measured from a frequency sweep at small deformations. The purpose of this study was to investigate evaluation of the cross-over point in the amplitude sweep as a measure of flexibility for the OBT family of products. This measurement can characterize dermal fillers and explain their differentiating features and behavior in the skin.

b) Test Methods

Figure 3B:
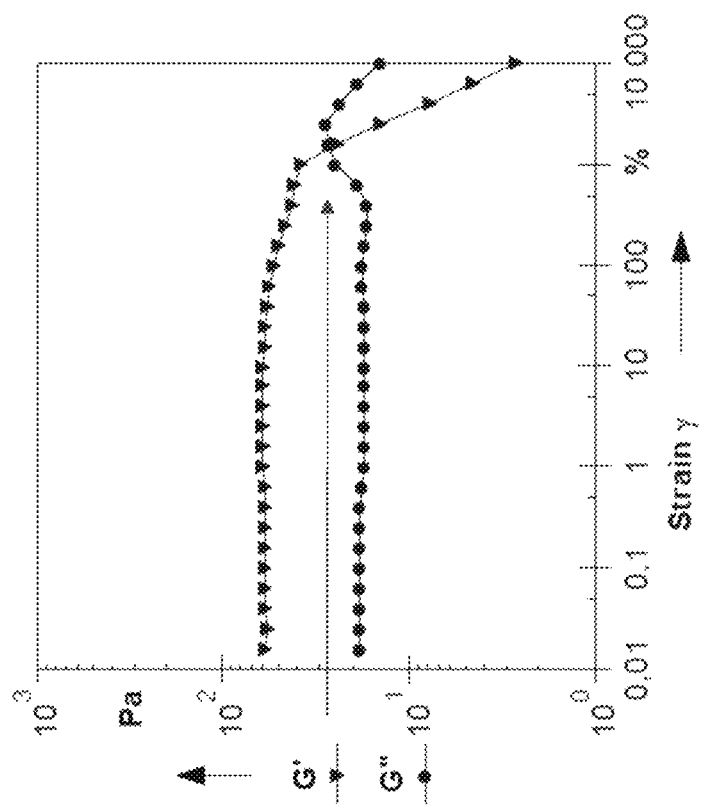
FIG. 3 shows an amplitude sweep results for Defyne (FIG. 3a) and Refyne (FIG. 3b).
Figure 3A:
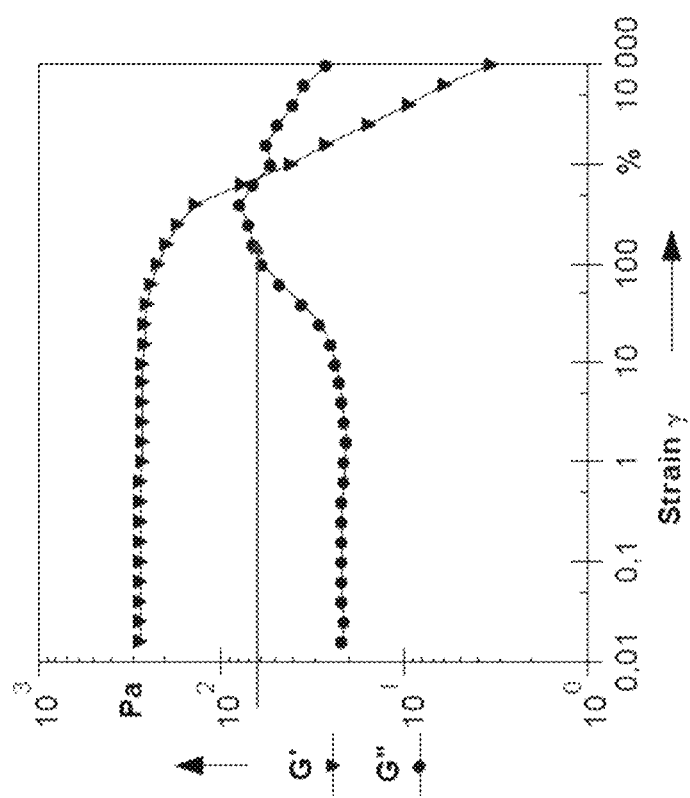

The rheology measurement was performed in a sequence including a relaxation time of 30 min, a frequency sweep from 10 to 0.1 Hz at 0.1% strain, followed by an amplitude sweep from 0.1 to 10000% (0.001 to 100) strain at 1 Hz. The gap was 1 mm using a PP25 measuring system at 25° C. The frequency sweep was evaluated for G', G" at 0.1 Hz. The amplitude sweep was first evaluated at 0.1% strain in order to verify that the applied frequency sweep strain was within the linear viscoelastic range. Secondly the strain was evaluated at the crossover point of the amplitude sweep, i.e. the point where G' and G" have the same value (FIG. 3).

c) Test Results

Figure 4:
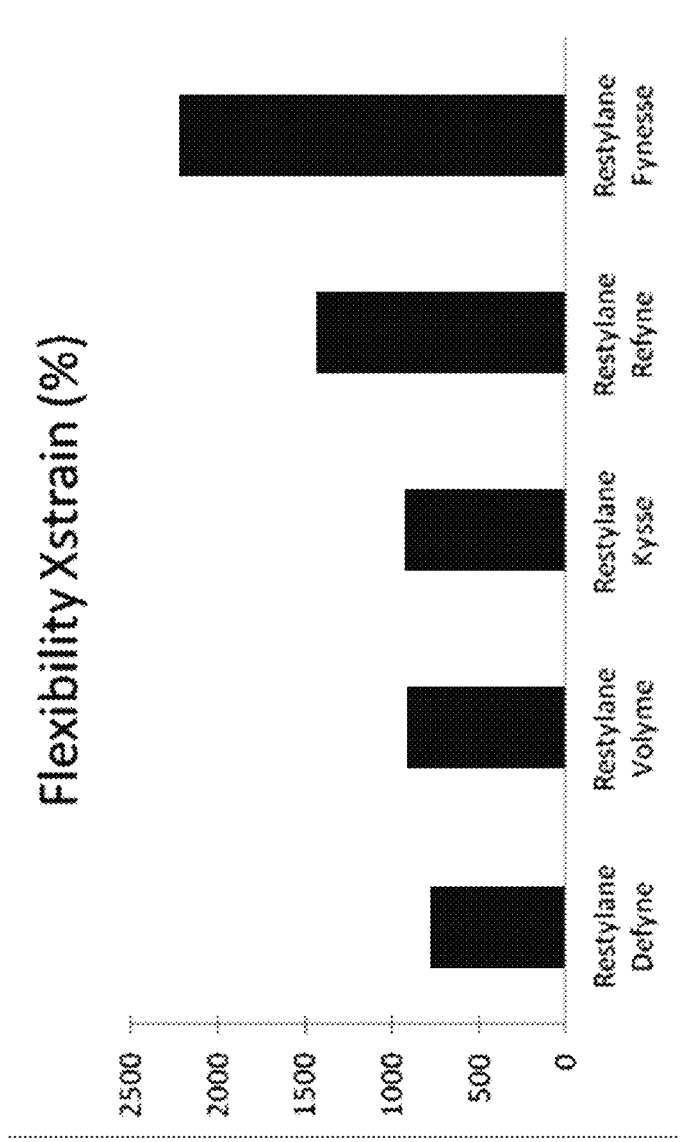
FIG. 4 shows flexibility values for a number of dermal fillers.

Each product of the OBT range (Table 1) was analyzed for the xStrain value derived from the amplitude sweep (FIG. 4).

TABLE 1

List of analyzed products and test results:

| Product | xStrain (%) |
|---|---|
| Restylane Defyne | 761 |
| Restylane Volyme | 908 |

TABLE 1-continued

List of analyzed products and test results:

| Product | xStrain (%) |
|---|---|
| Restylane Kysse | 930 |
| Restylane Refyne | 1442 |
| Restylane Fynesse | 2221 | d) Discussion

Since the different products in the OBT family are crosslinked in exactly the same way, differing only in the amount of crosslinker used, it can be assumed that the main difference in the crosslinking structure is the distance between crosslinking points (FIG. 5). From this follows that when the material is subjected to mechanical stress, the material with a larger distance between the crosslinking points will allow more deformation before the HA chains are fully stretched (FIG. 6). This material will be perceived as more flexible, elastic or compliant, compared to a material with smaller distance between crosslinking points. Materials with larger distance between the crosslinking points—everything else equal—will tend to be more flexible, and will also tend to be softer. It must be pointed out, however, that the firmness derived from the small-deformation frequency sweep is a completely different property from the flexibility derived from the large-deformation amplitude sweep. Just because a material is soft, it does not necessarily have to be flexible. Each property has to be measured separately.

The person skilled in the art realizes that the present invention by no means is limited to the preferred embodiments described above. On the contrary, many modifications and variations are possible within the scope of the appended claims. Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A process for evaluating flexibility of an injectable gel, the process comprising:
   subjecting the injectable gel to oscillating mechanical stresses to determine elastic modulus (G') and viscous modulus (G") of the injectable gel as a function of strain ($\gamma$) in an amplitude sweep of the injectable gel;
   determining the strain ($\gamma_{cross}$) at a crossover point of the amplitude sweep of the injectable gel, wherein the crossover point of the amplitude sweep is where G' and G" have the same value;
   determining the flexibility of the injectable gel as the strain $\gamma_{cross}$ at the crossover point; and
   comparing the flexibility of the injectable gel with a flexibility value of a reference gel, wherein flexibility of the injectable gel higher than the flexibility value of the reference gel indicates that the injectable gel is more suitable than the reference gel for being implanted at facial regions that are subjected to movement.

2. The process according to claim 1, wherein the amplitude sweep is performed by increasing deformation of the injectable gel until a change in both G' and G" are observed.

3. The process according to claim 1, wherein determining the strain ($\gamma_{cross}$) at the crossover point of the amplitude sweep of the injectable gel is performed by plotting G' and G" as a function of the strain ($\gamma$) and selecting the crossover point as the point where the plot of G' and the plot of G" intersect.

4. The process according to claim 3, wherein plotting G' and G" as a function of the strain ($\gamma$) comprises performing a frequency sweep at a fixed strain before performing the amplitude sweep.

5. The process according to claim 1, wherein the flexibility of the injectable gel is measured in percentage (%).

6. The process according to claim 1, wherein the amplitude sweep is performed at a frequency of between 0.5 Hz-1.5 Hz.

7. The process according to claim 1, wherein the injectable gel is a dermal filler comprising crosslinked hyaluronic acid.

8. A method of comparing suitability of injectable gels as dermal fillers, the method comprising:
    evaluating the flexibility of a plurality of injectable gels that are candidate dermal fillers according to the method of claim 1;
    comparing the evaluated flexibility between or among the plurality of injectable gels; and
    selecting a dermal filler from the plurality of injectable gels as a dermal filler suitable for injection based on the comparison.

9. The method according to claim 8, wherein the injectable gel having the highest flexibility value of the plurality of injectable gels is selected as the dermal filler suitable for injection in the facial area.

10. The process according to claim 1, wherein determining the strain ($\gamma_{cross}$) at the crossover point of the amplitude sweep of the injectable gel, wherein the crossover point of the amplitude sweep is where G' and G" have the same value, comprises
    receiving input data of G' and G" as a function of the strain $\gamma$ of the injectable gel.

11. The process according to claim 10, further comprising displaying the flexibility of the injectable gel on a computer screen.

12. The process of claim 10, wherein the process is performed using a device in communication with computer-executable components run on a processing unit included within the device.

* * * * *